United States Patent
Zasuwa et al.

(10) Patent No.: US 11,458,233 B2
(45) Date of Patent: Oct. 4, 2022

(54) METHOD FOR DETECTING INTRAVASCULAR VOLUME DEPLETION DURING A HEMODIALYSIS SESSION

(71) Applicant: HENRY FORD HEALTH SYSTEM, Detroit, MI (US)

(72) Inventors: Gerard Zasuwa, West Bloomfield, MI (US); Stanley Frinak, Farmington Hills, MI (US); Jerry Yee, Beverly Hills, MI (US); Anatole Besarab, Bloomfield Hills, MI (US); John B. Kennedy, Evanston, IL (US); Jeffrey J. Sands, Orlando, FL (US)

(73) Assignee: Henry Ford Health System, Detroit, MI (US)

( * ) Notice: Subject to any disclaimer, the term of this patent is extended or adjusted under 35 U.S.C. 154(b) by 651 days.

(21) Appl. No.: 16/309,019

(22) PCT Filed: Jun. 13, 2017

(86) PCT No.: PCT/US2017/037243
§ 371 (c)(1),
(2) Date: Dec. 11, 2018

(87) PCT Pub. No.: WO2017/218529
PCT Pub. Date: Dec. 21, 2017

(65) Prior Publication Data
US 2019/0314566 A1 Oct. 17, 2019

Related U.S. Application Data

(60) Provisional application No. 62/349,380, filed on Jun. 13, 2016.

(51) Int. Cl.
*A61M 1/16* (2006.01)

(52) U.S. Cl.
CPC ....... *A61M 1/1603* (2014.02); *A61M 2205/18* (2013.01); *A61M 2205/3303* (2013.01);
(Continued)

(58) Field of Classification Search
CPC ............ A61M 1/1603; A61M 2205/18; A61M 2205/3303; A61M 2205/3344;
(Continued)

(56) References Cited

U.S. PATENT DOCUMENTS

| 6,585,675 B1 | 7/2003 | O'Mahony et al. |
| 8,348,850 B2 | 1/2013 | Frinak et al. |

(Continued)

FOREIGN PATENT DOCUMENTS

| EP | 1419396 B1 | 8/2014 |
| WO | 2011081740 A1 | 7/2011 |
| WO | 2014107656 A1 | 7/2014 |

OTHER PUBLICATIONS

Extended European Search Report for Application No. 17813930.9, dated Dec. 17, 2019, 8 pages.
(Continued)

*Primary Examiner* — Ariana Zimbouski
(74) *Attorney, Agent, or Firm* — Brooks Kushman P.C.

(57) ABSTRACT

A method of detecting intravascular volume depletion in a patient during a hemodialysis session includes measuring venous drip pressure for the patient. With a computer-driven analyzer, the method further includes analyzing the venous drip pressure and automatically and continuously determining a venous access pressure in proximity to a location of needle insertion into a vascular access site of the patient, wherein changes in venous access pressure are representative of changes in intravascular blood pressure. Using the analyzer, the method further includes comparing the venous access pressure to a standard and, if the venous access (Continued)

pressure is outside of a defined range of the standard, determining with the analyzer that the patient is experiencing intravascular volume depletion during the hemodialysis session.

14 Claims, 2 Drawing Sheets

(52) U.S. Cl.
CPC ............. *A61M 2205/3344* (2013.01); *A61M 2205/3386* (2013.01); *A61M 2205/50* (2013.01); *A61M 2230/30* (2013.01)

(58) Field of Classification Search
CPC ...... A61M 2205/3386; A61M 2205/50; A61M 2230/30
See application file for complete search history.

(56) References Cited

U.S. PATENT DOCUMENTS

| | | | |
|---|---|---|---|
| 2003/0136181 A1 | 7/2003 | Balschat et al. | |
| 2006/0272421 A1* | 12/2006 | Frinak | A61M 1/3659 |
| | | | 73/710 |
| 2007/0255112 A1* | 11/2007 | Taepke, II | A61N 1/37258 |
| | | | 600/300 |
| 2009/0088683 A1 | 4/2009 | Roger et al. | |
| 2013/0006128 A1 | 1/2013 | Olde et al. | |
| 2016/0325034 A1* | 11/2016 | Wiktor | A61M 1/3667 |

OTHER PUBLICATIONS

International Search Report and Written Opinion for Application No. PCT/US2017/037243, dated Sep. 19, 2017, 12 pages.
International Preliminary Report on Patentability for Application No. PCT/US2017/037243, dated Dec. 27, 2018, 7 pages.

* cited by examiner

METHOD FOR DETECTING INTRAVASCULAR VOLUME DEPLETION DURING A HEMODIALYSIS SESSION

CROSS-REFERENCE TO RELATED APPLICATIONS

This application is the U.S. National Phase of PCT/US2017/037243 filed Jun. 13, 2017, which claims the benefit of U.S. provisional application Serial No. 62/349,380 filed Jun. 13, 2016, the disclosures of which are hereby incorporated in their entirety by reference herein.

TECHNICAL FIELD

Embodiments relate to a system and method for detecting intravascular volume depletion during a hemodialysis session by measurement of venous access pressure.

BACKGROUND

Patients with end stage renal disease (ESRD) depend upon regular renal replacement therapy for survival. Typically, non-transplanted ESRD patients receive either hemodialysis or peritoneal dialysis therapy to remove accumulated waste products and excess fluid. Hemodialysis, in particular, is typically performed three times weekly for approximately 3 to 5 hours. The process of hemodialysis removes waste products by diffusion and convection and fluid removal is accomplished by ultrafiltration. During the process of ultrafiltration, fluid is removed from the extracellular space in sufficient quantity to decrease the patients' pre-dialysis weight to their so-called "estimated dry weight" as prescribed by their physician. This weight target is frequently modified for individual treatments based upon the pre-dialysis nursing assessment of the patient including assessment of the patients' clinical status, blood pressure, presence of edema, change in the patients' weight since the end of the previous hemodialysis treatment, their previous post-hemodialysis treatment blood pressure and their tolerance of the previous hemodialysis treatment. A typical ultrafiltration goal is for the removal of 2 Kg-4 Kg (i.e. 2-4 L) of fluid during the hemodialysis treatment. Ultrafiltration during hemodialysis removes fluid from the intravascular space which contains only approximately 5 L of blood (intravascular volume).

Therefore, maintenance of intravascular volume during ultrafiltration relies upon of refilling of the vascular space from movement of extracellular fluid into the vascular space. If refilling is inadequate, the patient will develop intravascular volume depletion which may result in physiologic responses such as vasoconstriction or increased heart rate in an attempt to maintain cardiac output and adequate blood pressure. Frequently, however, the patient may not be able to adequately compensate for rapid ultrafiltration and may develop signs or symptoms including cramping, dizziness or hypotension. In fact, intradialytic hypotension (IDH) is a frequent complication of hemodialysis and has been reported to occur during 5%-30% of all hemodialysis treatments and is a frequent source of morbidity (Sands J J et al., Hemodial Int. 2014 Apr; 18(2): 415-22). If severe or left untreated, IDH can result in loss of consciousness, circulatory collapse or even death. Early recognition of intravascular volume depletion is important to allow clinical personnel to provide interventions to prevent these patient complications. Such interventions may include decreasing the ultrafiltration rate, administration of IV saline, lowering patients' heads and raising their legs to increase central vascular volume, increasing dialysate (Na, etc.) in an effort to maintain patients' blood pressure, protect their cardiac output and correct their volume status.

In hemodialysis facilities, the current standard of care is to obtain blood pressure measurements and assess the patient clinically every 30 min. This, however, may be insufficient to identify early signs of intravascular volume depletion and to prevent hypotensive episodes. For this reason, clinicians have utilized other measures such as changes in relative blood volume during hemodialysis treatments to help guide volume removal and identify patients at risk for developing hypotension. These measures, however, are often difficult to interpret and are not routinely available in most hemodialysis facilities. Similarly, measurements of cardiac output and peripheral resistance are not available in hemodialysis facilities and with current technology cannot be feasibly performed throughout every hemodialysis treatment, even in research facilities.

SUMMARY

In one embodiment, a method of detecting intravascular volume depletion in a patient during a hemodialysis session includes measuring venous drip pressure for the patient. With a computer-driven analyzer, the method further includes analyzing the venous drip pressure and automatically and continuously determining a venous access pressure in proximity to a location of needle insertion into a vascular access site of the patient, wherein changes in venous access pressure are representative of changes in intravascular blood pressure. Using the analyzer, the method further includes comparing the venous access pressure to a standard and, if the venous access pressure is outside of a defined range of the standard, determining with the analyzer that the patient is experiencing intravascular volume depletion during the hemodialysis session.

In another embodiment, a method of detecting intravascular volume depletion in a patient during a hemodialysis session includes measuring venous drip pressure for the patient. With a computer-driven analyzer, the method further includes analyzing the venous drip pressure and automatically and continuously determining a venous access pressure in proximity to a location of needle insertion into a vascular access site of the patient, wherein changes in venous access pressure are representative of changes in intravascular blood pressure. The method further includes repeating the measuring, analyzing and determining steps to determine a plurality of venous access pressure values and calculate a moving average of venous access pressures and, using the analyzer, comparing the moving average of venous access pressures to a standard. If the moving average of venous access pressures is outside of a defined range of the standard, the method includes determining with the analyzer that the patient is experiencing intravascular volume depletion during the hemodialysis session.

In another embodiment, a method of detecting intravascular volume depletion in a patient during a hemodialysis session includes measuring venous drip pressure for the patient. With a computer-driven analyzer, analyzing the venous drip pressure and automatically and continuously determining a venous access pressure in proximity to a location of needle insertion into a vascular access site of the patient, wherein changes in venous access pressure are representative of changes in intravascular blood pressure. Using the analyzer, the method further includes comparing the venous access pressure to an initial, baseline value determined for the venous access pressure at a starting point of the hemodialysis session and, if the venous access pressure decreases by at least 50% below the baseline value, determining with the analyzer that the patient is experiencing intravascular volume depletion during the hemodialysis session.

DETAILED DESCRIPTION

As required, detailed embodiments of the present invention are disclosed herein; however, it is to be understood that the disclosed embodiments are merely exemplary of the invention that may be embodied in various and alternative forms. Therefore, specific structural and functional details disclosed herein are not to be interpreted as limiting, but merely as a representative basis for teaching one skilled in the art to variously employ the present invention.

Figure 1:
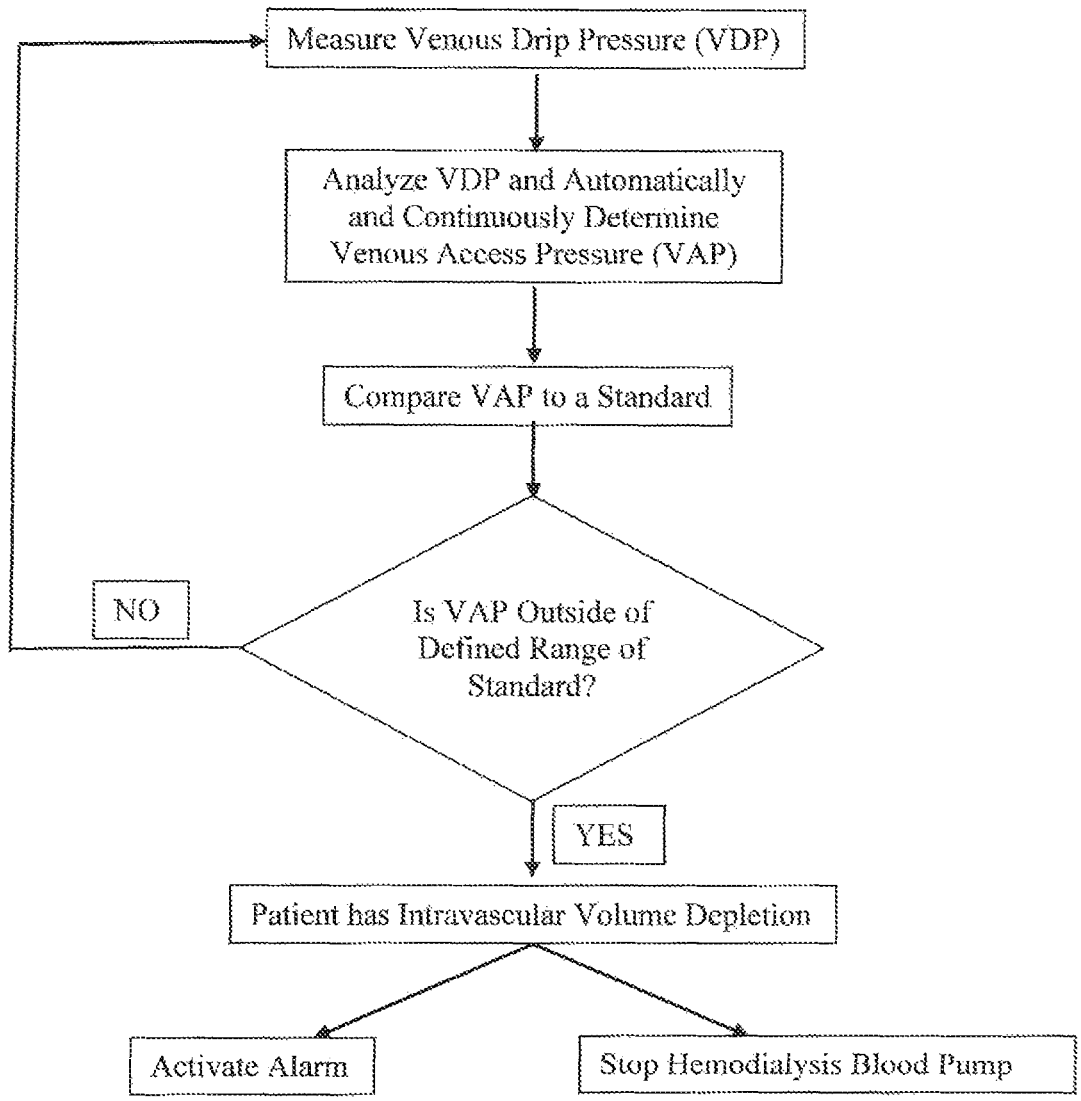
FIG. 1 is a flow chart depicting a method of detecting intravascular volume depletion during a hemodialysis session.

With reference to FIG. 1, a method of detecting intravascular volume depletion in a patient during a hemodialysis session includes measuring venous drip pressure (VDP) of the dialysis machine of the patient undergoing hemodialysis, and analyzing the VDP and automatically and continuously determining a venous access pressure (VAP) in proximity to a location of needle insertion into a vascular access site of the patient. Changes in VAP are representative of changes in intravascular blood pressure. The method further includes comparing the VAP to a standard and, if the VAP is outside of a defined range of the standard, determining that the patient is experiencing intravascular volume depletion during the hemodialysis session and potential vasoconstriction, hypotension and/or decreased cardiac output. The method may further include alerting the patient and/or medical personnel of intravascular volume depletion during a hemodialysis session.

The method disclosed herein identifies patients with potential intravascular volume depletion by identifying changes in the patients' physiologic response, allowing an alert to medical personnel to reevaluate the patient's volume status. This is based upon the continuous calculation of VAP. The determination of VAP separates important, novel information from VDP which is measured for the patient on hemodialysis machines.

According to the disclosed method, VAP is used to identify intravascular volume depletion. VAP is the measurement of the pressure in the venous section of the hemodialysis patient's arterio-venous access and reflects the rate of blood flow in the access (access flow). Approximately 80%-90% of hemodialysis patients have a surgically created vessel, i.e. an arterio-venous (AV) access in their arm or leg which is used to provide blood for hemodialysis. During hemodialysis, blood is removed and returned continuously through needles from the access at approximately 400 mL/min. AV accesses come in two varieties: 1) An AV fistula (AVF), a large blood vessel which is surgically created by the anastomosis of a patient's native artery to a native vein, or 2) An AV graft (AVG) which is a surgically implanted prosthetic vessel connecting an artery and vein.

AVF's and AVG's have high blood flows averaging approximately 600-1800 mL/min and, in some instances, may exceed 2 L/min or approximately 20% of cardiac output. Access flow, however, is not static and the rate will vary throughout hemodialysis. The access blood flow creates pressure in the access (VAP) which is determined continuously by the disclosed method. Thus, a change in VAP will reflect changes in the rate of access flow. A change in VAP is also representative of a change in intravascular blood pressure, as hypotension due to intravascular volume depletion will also cause a decrease in access pressure. This allows the system to provide a new and previously unrecognized window into a patient's physiologic response to intravascular volume depletion.

The method disclosed herein uses decreases in VAP during a hemodialysis session to provide real-time alerts of potential intravascular volume depletion. In response to intravascular volume depletion, the body may respond by peripheral vasoconstriction, and the patient may develop decreased cardiac output or hypotension. Each of these three events (vasoconstriction, decreased cardiac output and intradialytic hypotension) may result in a decrease in access flow and will be reflected by a decrease in intravascular blood pressure or VAP. The method disclosed herein identifies these VAP changes, and may trigger a machine alert/alarm to allow timely medical assessment of the patient's blood pressure and volume status to allow interventions as necessary. Since the VAP measurement disclosed herein is a continuous process, the disclosed method may provide alerts at any time during a hemodialysis session and not just at the time of routine, every half-hour blood pressure measurements and patient checks that is the standard of care in U.S. dialysis facilities.

With reference to U.S. Pat. No. 8,348,850 to Frinak et al. ("the '850 patent), incorporated by reference herein in its entirety, a false positive reading for the venous needle dislodgement device disclosed in the '850 patent could occur for physiological reasons related to a decrease in intravascular volume, potentially caused by potential vasoconstriction, hypotension and/or decreased cardiac output. Therefore, instead of dismissing the alarm as false if the needle is not dislodged, physiological reasons should be investigated as a potential cause. As such, the method described herein for detecting instances of intravascular volume depletion and alerting medical staff of this condition provides a very valuable diagnostic tool.

According to embodiments, a system and method are provided for detecting variations in VAP. The system includes an analyzer for automatically and continuously analyzing VDP, determining VAP, and comparing the determined VAP to a standard, whereby variations in the VAP outside of the range of a standard may be indicative of an abnormality. The system as disclosed herein may include, but is not limited to, any system that is able to detect variations in VAP. An example of such a system is a hemodialysis machine.

Alternatively, the system can include a hand-held device. In this embodiment, a pressure gauge can be replaced with a hand-held microprocessor-controlled device that measures and records the pressure measurements. An algorithm calculates the average pressure over a predetermined sampling period. The system may also contain a computer database to recall individual patient information and to record current pressure measurements in the patient's database record. Data from the system can be transferred via a communication port to a larger computer system with a more extensive patient database.

The "analyzer" as used herein may include a device that is capable of automatically analyzing VDP and deriving VAP. Such an analyzer can be computer-driven. For example, the analyzer can include a device that is associated with a hemodialysis machine, such that it automatically and continuously determines VAP during a hemodialysis session. The analyzer can then compare VAP to a standard. An equation may be used that estimates pressure inside a blood access site. In one embodiment, this equation calculates the ratio between venous blood pressure and mean arterial pressure. The analyzer may be associated with a hemodialysis machine, or with any other device with blood flow. The analyzer may include an algorithm that analyzes VAP to identify patients at risk for intravascular volume depletion.

The term "communication device" as used herein may include a device operably connected to the system for communicating a warning. The communication device can be selected from, but is not limited to, electronic communications, a facsimile, a telephone, a cable modem, and a T1 connection.

The term "algorithm" as used herein may encompass any computation that enables an individual to ascertain the information necessary for detecting intravascular volume depletion. In one embodiment, the algorithm is computer-driven. The algorithm can be used as part of an integrated circuit. This circuit enables the algorithm to be more easily incorporated into a hemodialysis machine. The circuit can be created using technology known to those with skill in the art.

As described above, VDP is the pressure that is actually measured in the extracorporeal circuit (outside the body). The VDP is analyzed and then VAP is continuously determined in proximity of a location of venous needle's point of access on the body. The derived VAP is compared to a standard that can be set for the system, or derived from prior measurements of VAP during the hemodialysis session or from prior sessions for the patient. Each of the measuring, analyzing and deriving, and comparing steps may be repeated multiple times during the hemodialysis session, such that multiple VAP values may be determined over multiple time periods. The system may include an alarm that is activated and alerts medical personnel to a problem with the patient when intravascular volume depletion is detected.

According to an embodiment, the method calculates the actual pressure as seen at the tip of the needle by removing the pressure caused by the needle and tubing ($VDP_0$) from the measured VDP, which leaves VAP. By building the algorithm into the hemodialysis machine so that VAP is calculated continuously, an alarm can be sounded when VAP is abnormal as compared to a standard. In one embodiment, the method includes turning off a blood pump of the hemodialysis machine if intravascular volume depletion is detected.

The algorithm can be utilized as an alarm system in any device that transports blood from a patient to an extracorporeal circuit and returns the blood to the patient. The algorithm determines the pressure at the point of insertion of the blood into the body based on a pressure reading in the extracorporeal blood circuit along with the rate of fluid flow through the device, the physical properties of the fluid transported through the device and a determination of the pressure inherent in the external circuit beginning from the pressure measuring device to the end of the needle at the point of insertion into the body. The algorithm allows the alarm level to vary with the rate of fluid flow through the device. The device can be utilized as an alarm in plasmapheresis, heart lung machines and any extracorporeal blood treatment or infusion technology circuits. Alarm systems based on the device are not limited to medical applications but can be developed for any fluid transporting device. Alarm levels can be set at any pressure value that provides safe operation of the device.

The alarm can be a wireless alarm or a hardwired alarm. More specifically, a wireless alarm can send wireless signals to a portable, handheld monitor/device that is carried by medical personnel or a patient, or to a central monitoring area, such as by the Internet or through communication mechanisms that include, but are not limited to electronic communications, facsimile, telephone, cable modem, and T1 connection. A hardwired alarm can send signals to any device that is in electrical connection with the system, such as a central monitoring area. The alarm can also be an audible warning or other similar signal that sends a command to the medical device (such as turn off) and/or wakes up the patient and alerts medical personnel.

The system can be used to monitor any type of patient blood access site for intravascular volume depletion. The types of blood access sites that can be monitored include, but are not limited to, fistulas, grafts, catheters, or any type of permanent blood access port. Intravascular volume depletion can be detected by the algorithm and a warning can be issued once a deviation from a defined standard level is exceeded.

Further, the system and method can be utilized to describe the relationship between blood flow, pressure, and hematocrit in any type of system that removes blood from a patient and returns the same blood to the patient. Thus, it can be used in conjunction with a heart-lung machine to determine alarm parameters for blood withdrawal and reinfusion. The system can also be used with intravenous infusion systems to determine the pressure profile for fluid infusion through a known tubing set and needle.

For the assessment of intravascular volume depletion, the standard may be an initial, baseline value of VAP determined at a starting point of the hemodialysis session, after the patient is cannulated and the blood pump started. The determined VAPs can then be compared to the baseline value of VAP throughout the session, wherein an alarm condition will occur if VAP is outside of a specified range of the baseline. In one embodiment, outside of a range of the standard would be if VAP decreases by at least 50% below the baseline value, and the method will detect that the patient is experiencing intravascular volume depletion during the hemodialysis session. Of course, other ranges are also contemplated.

The standard could also be a rate of change in VAP over time (i.e., slope). In scenarios involving venous needle dislodgement, the access pressure decreases extremely rapidly, such as in a matter of seconds, due to all the blood which should be flowing into the access instead being accidentally discharged outside of the body. As such, a large negative slope results in that situation. In the case of intravascular volume depletion, a negative slope will also result, but over a much more gradual period of time due to the fluid removal rate from the blood through the dialyzer being greater than the fluid refill rate from the body into the blood. A range would then be set with respect to a value of the slope, and the method will detect that the patient is experiencing intravascular volume depletion during the hemodialysis session if a slope is calculated outside of the defined range.

Due to the physiological processes involved in intravascular volume depletion, the decrease in intravascular blood pressure, and therefore VAP, will occur over a longer portion of the hemodialysis session as compared to an acute event such as venous needle dislodgement. Accordingly, in one embodiment, VAP is compared to the standard over a time period of at least 10% of a total period of the hemodialysis session. For example, if the dialysis session length is 3 hours, then VAP may be compared to the standard over a time period of at least 18 minutes. According to the disclosed method, individual values of VAP may be compared to the standard, or alternatively a moving average of VAP over a selected period of time (e.g., between about 10 seconds to about 60 seconds) can be calculated and compared to the standard, which may smooth out minor variations in pressure over time.

Figure 2:
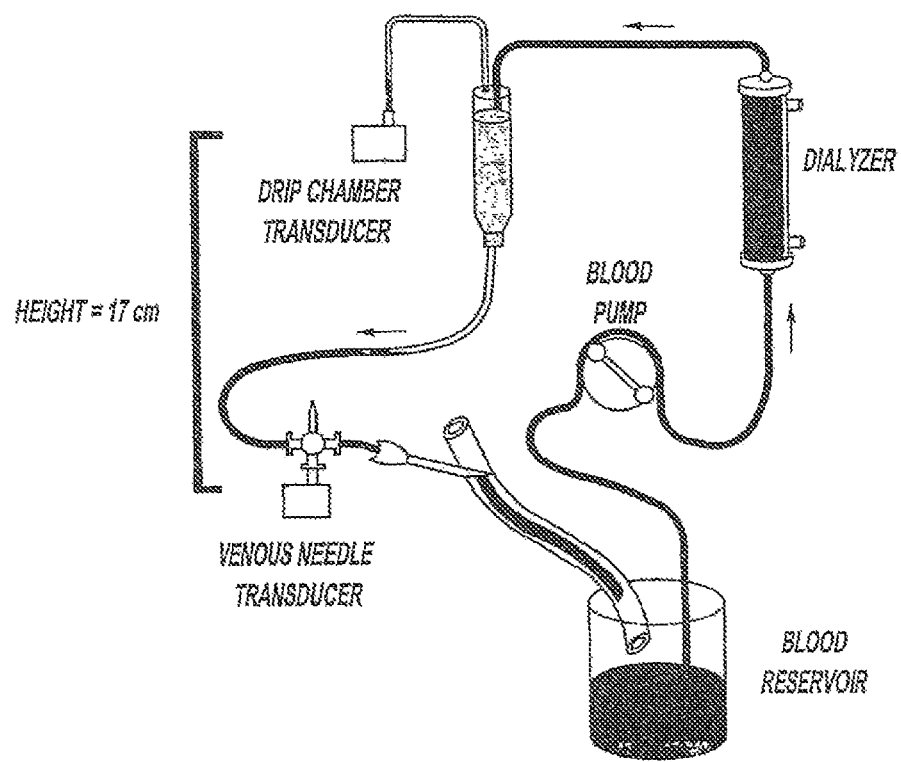
FIG. 2 illustrates a dialysis circuit used to determine the relationship between blood flow and hemodialysis machine venous drip chamber pressure.

The method according to an embodiment includes a technique termed the venous access pressure ratio test (VAPRT), where an experimental set-up is illustrated in FIG. 2. During hemodialysis, blood is drawn from the vascular access through the arterial needle by the hemodialysis machine blood pump. After passage through the dialyzer, the blood traverses the venous drip chamber and returns to the access through the venous needle. The pressure required to infuse blood back into the access through the venous tubing and access needle and to overcome the pressure within the access is recorded as the venous drip chamber pressure (VDP). As described above, one component of VDP is the access pressure in proximity to the venous needle site (VAP). Another component of VDP is the combined pressure required to overcome the resistance to flow through the tubing distal to the drip chamber (low) and through the venous return needle (high). VDP is also a function of needle size, tubing length and blood viscosity, represented by hematocrit. If the venous pressure within an access at the needle site is 0 mmHg, VDP can be defined as $VDP_0$, i.e., the venous drip chamber pressure when the access pressure is zero. Consequently, $VDP_0$ can be calculated for a given hemodialysis machine, tubing set, and needle size when the blood flow rate and hematocrit are measured. Once $VDP_0$ is determined, VAP can be calculated from the measured VDP.

$$VAP=VDP-VDP_0 \quad (1)$$

To normalize variations in VAP attributed to changes in mean arterial pressure (MAP), the venous access pressure ratio (VAPR) is calculated by dividing VAP by MAP.

$$VAPR=VAP/MAP \quad (2)$$

The data that yields the determination of $VDP_0$ may be contained within a central database repository that holds dialysis laboratory data and parameters acquired from hemodialysis machines that directly communicate with computers in the dialysis units. The VAPRT algorithm utilizes an empirical formula to calculate VAP from a dynamic measurement of VDP obtained at treatment and digitally recorded. An abnormal VAPRT has been operationally defined as VAPR>0.55 at three treatments.

Analysis of the data for the hemodialysis machine circuit yields the following second order polynomial equation:

$$VDP_0=0.00042*Qb^2+(0.62116*Hct^2+0.01203*Hct+0.12754)Qb-17.32509 \quad (3)$$

The common average intercept, −17.32509, was established empirically and is related to the 17 cm difference in height between the needle and drip chamber transducer at Qb=0. When pressure is measured from the transducer proximal to needle, the offset becomes zero, and the relationship between pressure and flow remains curvilinear. Thus, $VDP_0$ increases in relationship to increasing Qb and hematocrit.

Equation (3) can be used to calculate $VDP_0$ for any Qb at known Hct. For example, at Qb=500 ml/min and Hct 18.2%, $VDP_0$ is 163 mmHg and increases to 200 mmHg when Hct=38.4%. VAP can be calculated from VDP recorded at HD by Equation (1) and VAPR is calculated by Equation (2). At Hct 38.4%, Qb 500 ml/min, VDP 265 mmHg, $VDP_0$ 200 mmHg, and MAP 100 mmHg, VAPR=0.65=(265−200)/100. In the case where blood flow (Qb) is equal to zero in Equation (3), the following occurs:

$$VDP_0=0+0-17.32509=17.32509$$

Venous access pressure (VAP) is then calculated using Equation (1).

$$VAP=VDP-VDP_0 \quad VAP=VDP-(-17.32509)$$
$$VAP=VDP+17.32509$$

The constant (−17.32509) is determined by the dialysis machine type and the level of the patient's access site. Clinical studies have shown that the venous drip chamber pressure recorded by the machine and corrected for the height difference between the drip chamber transducer the patient's access gives an accurate value for venous access pressure. The venous drip chamber pressure recorded by the machine and corrected for the height difference between the drip chamber transducer the patient's access gives an accurate value for venous access pressure. The algorithm can therefore be incorporated into the dialysis machine, and the dialysis machine automatically records the readings. Additionally, a sensor can be placed on the hemodialysis machine to determine the height difference between the venous drip chamber transducer and the level of the patient's access site.

The VAPRT relies on a nonlinear regression formula to calculate $VDP_0$ for specific hemodialysis blood tubing set and access needle when the patient's hemodialysis blood pump flow (Qb) and hematocrit are known. The formula was developed from data analysis obtained during in vitro sham hemodialysis. The experimental dialysis machine (Fresenius 2008H, Lexington, Mass., U.S.A.) blood pump was calibrated prior to experiments using the standard maintenance procedure. The exact flow was not measured during the in vitro experiment as the intention a priori was to design a monitoring system that utilized routine dialysis data obtained from each dialysis treatment. The reservoir is filled with 500 ml of human whole blood obtained from the hospital blood bank. The blood pump transports blood from a reservoir through the dialyzer and the venous drip chamber and then to a 15 gauge, 1-inch backeye access needle. The venous access needle is inserted into a section of large-bore tubing that is open at both ends. One end of the tubing returns blood to the reservoir and the other end is elevated to prevent blood from escaping. This section of the circuit is not designed to simulate an actual access, but to avoid any resistance to flow at the tip of the venous access needle that can be recorded as an increase in VDP. The access needle is positioned 17 cm below the venous drip chamber transducer to simulate the average location of an angioaccess relative to the transducer during a typical hemodialysis treatment. The drip chamber transducer monitors the pressure created by the blood flowing through the circuit. $VDP_0$ readings are obtained directly from the hemodialysis machine. A sample of blood is obtained for hematocrit determination from the reservoir. $VDP_0$ is recorded as Qb is increased from 0 to 600 ml/mm in 50 ml/mm increments. A separate transducer, placed directly behind the access needle, measures the pressure created by the access needle's intrinsic resistance. The blood is then diluted with matched human plasma to lower hematocrit by approximately 4%. Blood is permitted to circulate at 500 ml/mm for 5 minutes to ensure uniform mixing with the additional plasma before the next sample is obtained for hematocrit measurement. $VDP_0$ measurements are repeated for Qb from 0 to 600 ml/mm. The circulated blood is diluted five times, reducing the original hematocrit by approximately 20 percentage points. $VDP_0$ measurements were conducted at each of the five dilutions.

The algorithm calculates VAPR from VDP and blood pump flow data that is routinely collected during hemodialysis and stored in a computer database. To limit variability intrinsic to differences in needle gauge, patients with less than 48 hemodialysis treatments were eliminated from analysis because a smaller gauge needle is frequently used when initially cannulating a new or poorly developed angio-access. The program extracts the most recent hematocrit and individual treatment data from the computer database and analyzes data for those patients who receive treatments via a graft. The VAPR is calculated each time the blood pressure is measured during hemodialysis, given the following criteria: $Qb \geq 200$ ml/mm, $VDP \geq 20$ mmHg and $MAP \geq 75$ mmHg. Data from the last hour of hemodialysis is excluded to eliminate the effect of ultrafiltration on hematocrit (elevated blood viscosity), blood pressure, and changes in systemic and vascular access resistances. The algorithm then calculates the mean VAPR for each hemodialysis treatment using all available data. In the majority of cases, three or four measurements are available. Patients with <10 hemodialysis treatments during a month were excluded. The VAPRT is considered positive when, starting with the eighth treatment of the month; the program determines that the VAPR exceeds the specified cutoff value during three consecutive treatments.

Mathematical modeling of $VDP_0$ data was accomplished by fitting each individual curve with an equation of the form:

$$VDP_0 = A*Qb^2 + B*Qb + C \quad (1a)$$

The constant C represents the value of VDP when Qb=0 and the average value of −17.325 mmHg was used during further analysis of the data. Because coefficient A varied minimally from 0.0004232 to 0.0004327, an increase of only 1.5 mmHg in VDPQ at Qb=400, a mean value of 0.00042329 was used. Coefficient B varied the most with hematocrit from 0.145289 to 0.231968. The raw data was then fit with Equation (2a).

$$VDP_0 = 0.00042329*Qb^2 + B*Qb - 17.325 \quad (2a)$$

B coefficients were obtained for each hematocrit value and Equation (3a) was fit to the data.

$$B = 0.62116*Hct^2 + 0.01203*Hct + 0.12754 \quad (3a)$$

Equations (2a) and (3a) were combined to yield Equation (4a) that relates $VDP_0$ to Qb and Hct.

$$VDP_0 = 0.00042*Qb^2 + (0.62116*Hct^2 + 0.01203*Hct + 0.12754)*Qb - 17.32509 \quad (4a)$$

Equation (4a) was evaluated for accuracy using a nonlinear regression program (DataFit, Oakdale Engineering, Oakdale, Pa., U.S.A.). The adjusted coefficient of multiple determination $r^2 = 0.99982$ validated that Equation (4a) represents an accurate mathematical model of the pressure data for access monitoring by dynamic VAPRT.

As blood flow increases VDP increases, primarily attributed to augmented resistance created by the venous needle. Elevation of hematocrit also increases VDP. The variability in VDP values from Qb and hematocrit can be reduced if the measurements are made at a fixed, relatively low, blood flow. However, the appropriate warning level for VDP varies among individuals depending on the MAP and hematocrit. By using Equation (2) to calculate VAPR, the VAPRT adjusts the VDP warning level for each access pressure measurement in relationship to Qb, hematocrit and MAP. Presently, the algorithm is limited to 1 inch 15 gauge needles for cannulation until investigation of other needle gauges has been carried out.

The VAPRT does not require specific training and the algorithm examines data currently entered in the patient database and evaluates the patient's access for each dialysis treatment. The VAPRT calculates a VAPR for each dialysis treatment, rendering it ideal for trend analysis. To minimize spurious alarms, a triplet rule may be imposed whereby three consecutive treatments with an abnormal VAPR are necessary to elicit a warning.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of noninvasively monitoring intravascular volume depletion in a patient during a hemodialysis session, the method comprising:
   receiving a measured venous drip pressure for the patient;
   with a computer-driven analyzer, analyzing the venous drip pressure and automatically and continuously determining a venous access pressure in proximity to a location of needle insertion into a vascular access site of the patient, wherein changes in venous access pressure are representative of changes in intravascular blood pressure;
   using the analyzer, noninvasively monitoring the intravascular blood pressure by comparing the venous access pressure to a standard during a selected hemodialysis session over a time period of at least 10% of a total period of the selected hemodialysis session; and
   if the venous access pressure is outside of a defined range of the standard, determining with the analyzer that the patient is experiencing intravascular volume depletion during the selected hemodialysis session.

2. The method of claim 1, wherein the standard is an initial, baseline value of venous access pressure determined at a starting point of the hemodialysis session.

3. The method of claim 1, wherein the standard is a rate of change in the venous access pressure over time.

4. The method of claim 1, further comprising turning off a blood pump of a hemodialysis machine if intravascular volume depletion is detected.

5. The method of claim 1, further comprising activating an alarm that notifies at least one of the patient or medical personnel of the detected intravascular volume depletion.

6. The method of claim 1, wherein determining the venous access pressure includes correcting the venous access pressure based on a relative height of a drip chamber and for a viscosity of blood.

7. A method of noninvasively monitoring intravascular volume depletion in a patient during a hemodialysis session, the method comprising:
   receiving a measured venous drip pressure for the patient;
   with a computer-driven analyzer, analyzing the venous drip pressure and automatically and continuously determining a venous access pressure in proximity to a location of needle insertion into a vascular access site of the patient, wherein changes in venous access pressure are representative of changes in intravascular blood pressure;

repeating the receiving, analyzing and determining steps to determine a plurality of venous access pressure values and calculate a moving average of venous access pressures;

using the analyzer, noninvasively monitoring the intravascular blood pressure by comparing the moving average of venous access pressures to a standard during a selected hemodialysis session over a time period of at least 10% of a total period of the selected hemodialysis session; and if the moving average of venous access pressures is outside of a defined range of the standard, determining with the analyzer that the patient is experiencing intravascular volume depletion during the selected hemodialysis session.

8. The method of claim 7, wherein the standard is an initial, baseline value of venous access pressure determined at a starting point of the hemodialysis session.

9. The method of claim 7, wherein the standard is a rate of change in the venous access pressure over time.

10. The method of claim 7, further comprising turning off a blood pump of a hemodialysis machine if intravascular volume depletion is detected.

11. The method of claim 7, further comprising activating an alarm that notifies at least one of the patient or medical personnel of the detected intravascular volume depletion.

12. The method of claim 7, wherein determining the venous access pressure includes correcting the venous access pressure based on a relative height of a drip chamber and for a viscosity of blood.

13. The method of claim 2, wherein the defined range is a decrease of the venous access pressure of at least 50% below the standard.

14. The method of claim 1, wherein the venous drip pressure and the venous access pressure are related by a constant, and the comparing step includes comparing the venous access pressure or the related venous drip chamber pressure to the standard.

* * * * *